United States Patent [19]

Robinson

[11] Patent Number: 4,576,815

[45] Date of Patent: Mar. 18, 1986

[54] PROCESS FOR THE EXTRACTION OF METAL VALUES AND NOVEL METAL EXTRACTANTS

[75] Inventor: Frank Robinson, Gt. Manchester, England

[73] Assignee: Imperial Chemical Industries Limited, London, England

[21] Appl. No.: 541,120

[22] Filed: Oct. 12, 1983

[30] Foreign Application Priority Data

Jul. 7, 1983 [GB] United Kingdom ............... 8318412

[51] Int. Cl.$^4$ ............................................. B01D 11/00
[52] U.S. Cl. .................... 423/658.5; 423/24; 423/100; 423/139; 75/101 BE; 75/117; 544/224; 544/225
[58] Field of Search ............. 423/24, 100, 139, 658.5; 75/101 BE, 117; 544/224, 225

[56] References Cited

U.S. PATENT DOCUMENTS 3,086,973  4/1963  Nyholm .......................... 544/225

FOREIGN PATENT DOCUMENTS 57797  8/1982  European Pat. Off. .

OTHER PUBLICATIONS

R. Urban and O. Schnider, Helv. Chim. Acta, 41 1806 (1958) (see in particular pp. 1808 and 1813).
E. F. Godefroi, J. Org. Chem., 27 2264 (1962).

Primary Examiner—John Doll
Assistant Examiner—Robert L. Stoll
Attorney, Agent, or Firm—Cushman, Darby & Cushman

[57] ABSTRACT

Metal values are extracted from aqueous solutions of metal salts containing halide or pseudo halide ions by pyrimidine, pyrazine or pyridazine derivatives bearing the substituent $-(C=O.X)_n$ where X is the group $-OR_1$ or $-NR_2R_3$ and n is 1, 2 or 3. $R_1$ is a hydrocarbyl group containing from 1 to 36 carbon atoms and $R_2$ and $R_2$ together contain from 1 to 36 carbon atoms. The molecule as a whole contains from 5 to 36 alkyl carbon atoms and may carry further optional substituents. The process is especially useful for the recovery of metals from leach solutions derived from sulphur-containing ores.

8 Claims, No Drawings

PROCESS FOR THE EXTRACTION OF METAL VALUES AND NOVEL METAL EXTRACTANTS

This invention relates to a process for the extraction of metal values from aqueous solutions of metal salts, and in particular to a process for the extraction of metal values from aqueous solutions in the presence of halide anions.

The use of solvent extraction techniques for the hydrometallurgical recovery of metal values from metal ores has been practised commercially for a number of years. For example copper may be recovered from oxide ores or from ore tailings by treating the crushed ore with sulphuric acid to give an aqueous solution of copper sulphate which is subsequently contacted with a solution in a water-immiscible organic solvent of a metal extractant whereby the copper values are selectively extracted into the organic phase.

The application of solvent extraction techniques to aqueous solutions containing halide anions however has presented numerous technical problems. For example copper bearing sulphur-containing ores such as chalcopyrite may be leached using ferric chloride or cupric chloride solutions, but the solvent extraction of the resultant leach solutions presents formidable difficulties.

The present invention provides a process for the extraction of metal values from aqueous solutions containing halide ions by the use of metal extractants whose several properties meet the stringent requirements imposed on the extractant by the system.

According to the present invention there is provided a process for extracting metal values from aqueous solutions of metal salts containing halide or pseudo halide anions which comprises contacting the aqueous solution with a solution in a water-immiscible organic solvent of a substituted pyrimidine pyrazine or pyridazine of formula:

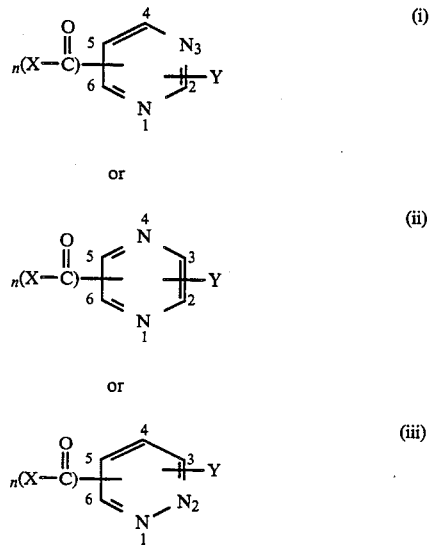

wherein

X is the group —$OR_1$ or —$NR_2R_3$, $R_1$ being a hydrocarbyl group containing from 1 to 36 carbon atoms and $R_2$ and $R_3$ separately being hydrogen or a hydrocarbyl group, and $R_2$ and $R_3$ together containing from 1 to 36 carbon atoms;

n is 1, 2 or 3; and

Y represents one or more groups which may separately be hydrogen, halogen, optionally substituted alkyl, optionally substituted aryl, alkoxy, aryloxy, aralkyl, carboxylic acid, cyano, and nitro;

provided that there is present in the molecule a total number of from 5 to 36 alkyl carbon atoms, The 5 to 36 alkyl carbon atoms which must be present in the molecule may be distributed between the groups $R_1$ and Y and the groups $R_2$, $R_3$ and Y respectively. Thus if Y is hydrogen or is a substituent containing no alkyl carbon atoms, then $R_1$ must contain from 5 to 36 alkyl carbon atoms or $R_2$ and $R_3$ together must contain from 5 to 36 carbon atoms respectively. However, if Y is a substituent containing one or more alkyl carbon atoms, the number of alkyl carbon atoms present in $R_1$ and in $R_2$ and $R_3$ respectively may be reduced accordingly.

Preferably at least one position ortho to one of the two nitrogen atoms in the pyrimidine, pyrazine or pyridazine ring is free from bulky substituents and preferably is free from any substituent. It is especially preferred that both positions ortho to at least one of the nitrogen atoms are free from bulky substituents, and preferably are free from any substituent. There is thus a general preference that one of the two nitrogen atoms in the pyrimidine, pyrazine or pyridazine ring is sterically unhindered, whilst the other nitrogen atom is sterically hindered by one or more adjacent substituents.

When n is 2 or 3, the substituent—X is the respective groups —COX may be the same or different. For example when n is 2, the two groups —COX may be —$COR_1$ and $COR_1'$ respectively where $R_1$ and $R_1'$ are both hydrocarbyl groups each containing from 1 to 36 carbon atoms, provided that the total number of alkyl carbon atoms in the molecule as a whole is from 5 to 36. As examples of suitable pyrazines wherein n is 2, there may be mentioned alkyl esters of 2,6-dicarboxypyrazine. As examples of suitable pyrimidines wherein n is 2, there may be mentioned alkyl esters of 4,5-dicarboxypyrimidine. As examples of suitable pyridazines wherein n is 2 there may be mentioned alkyl esters of 4,5-dicarboxypyridazine.

When n is 1, the group —COX is preferably located in the -5 position in the pyrimidine ring, since we have found that such compounds generally have superior hydrolytic stability. In the pyrazine ring the substituent —COX is of necessity in the -2 position.

Preferably the group(s) —Y are hydrogen or, more preferably, one or more alkyl groups, for example one or more lower alkyl groups or are one or more optionally substituted aryl groups. As optionally substituted aryl groups there may be mentioned the phenyl group and the phenyl group carrying as optional substituent one or more lower alkyl groups or lower alkoxy groups or one or more halogen atoms or one or more carboxylic acid or carboxylic acid ester groups. The presence of, for example an alkyl substituent, on the aryl group may provide enhanced solubility of the reagent in the water-immiscible organic solvent or may permit the use of a relatively shorter alkyl chain in the group —$OR_1$.

Pyrimidine compounds of the present invention having the group —COX in the preferred -5 position preferably have a substituent —Y in the -4 (or the equivalent -6) position, thereby increasing the steric hindrance of the nitrogen in the -3 (or the equivalent -1) position.

Similarly, pyrazine compounds of the present invention may have a substituent —Y in the -6 position to hinder the reactivity of the nitrogen in the -1 position, thereby favouring the formation of a metal complex through the nitrogen in the -4 position.

The substituted pyrimidine pyrazine and pyridazine compounds of the present invention may be prepared by conventional means. For example when X is the group —$OR_1$, they may be prepared by the reaction of the appropriate pyrimidine pyrazine or pyridazine carboxylic acid with the appropriate alcohol to form the desired ester. Alternatively, the lower esters, for example methyl or ethyl esters may be subjected to ester exchange reactions with higher alcohols, or the acid chlorides may be reacted with the appropriate alcohol or phenol.

When the group X is —$OR_1$, $R_1$ may for example be an alkyl group, for example an octyl, nonyl, decyl, dodecyl, tridecyl, pentadecyl, hexadecyl or octadecyl group or a higher alkyl group. $R_1$ may for example be a cyclo alkyl group such as cyclohexyl. $R_1$ may for example be an aryl, alkyaryl or alkoxyaryl group for example p-nonylphenyl or p-dodecylphenyl.

To achieve good solubility of the compound in preferred organic solvents, the alkyl solubilising group(s) (for example $R_1$) are preferably branched alkyl group(s) or a mixture (including an isomeric mixture) of branched alkyl groups. It is especially preferred that the molecule contains a total of from 9 to 24 alkyl carbon atoms.

Highly branched alkyl groups may be usefully derived from branched alcohols prepared by the Guerbet and Aldol condensations. Such alcohols are characterised by branching at the position beta to the hydroxyl group and have the general formula:

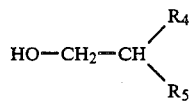

(iv)

wherein $R_4$ and $R_5$ are both alkyl groups and $R_4$ contains two fewer carbon atoms than $R_5$. $R_4$ and $R_5$ may be straight chain or branched chain alkyl groups and may be isomeric mixtures of alkyl groups. A mixture of highly branched alcohols may be obtained by Guerbrt or Aldol condensations of mixtures of alcohols and aldehydes respectively. By way of example, good solubility in preferred organic solvents is conferred on the pyrimidine pyrazine or pyridazine compounds wherein $R_1$ is derived from 2-hexyldecanol, 2-octyldodecanol and most especially commercial isooctadecanol prepared by the dimerisation of commercial nonanol or commercial nonaldehyde and believed to consist essentially of a mixture of geometrical isomers of the compound:

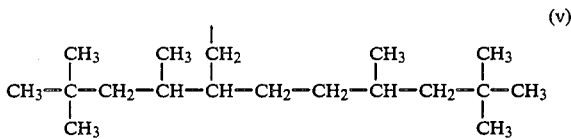

(v)

Alcohols of formula (iv) above, although branched, are all primary alcohols. For pyrazine compounds especially, there may be advantages in employing a group —$R_1$ derived from a branched secondary or tertiary alcohol, for example 3,9-diethyl-tridecan-6-ol.

The amide group —$NR_2R_3$ may be secondary ($R_3$ is hydrogen) or, more preferably, tertiary. $R_2$ and $R_3$, which may be the same or different, may be groups of the type indicated above for $R_1$. $R_2$ and $R_3$ taken together preferably contain from 15 to 36 carbon atoms. Thus $R_3$ may be for example a lower alkyl group, for example a methyl group, provided $R_2$ is correspondingly larger. $R_2$ and $R_3$ taken together are preferably alkyl groups containing a total of from 15 to 36 carbon atoms. For tertiary amines, sufficient solubility in preferred organic solvents may generally be achieved if $R_2$ and $R_3$ are straight chain or branched chain alkyl groups. However for secondary amides ($R_2$ is hydrogen), $R_3$ is preferably a branched chain alkyl group. The total number of alkyl carbon atoms in the molecule is from 5 to 36, and in consequence if alkyl carbon atoms are present in the substituent Y, the number of alkyl carbon atoms in $R_2$ and $R_3$ may be correspondingly reduced without loss of solubility.

The process of the present invention may be applied to the extraction from aqueous solutions containing halide or pseudohalide ion of any metal capable of forming a stable halide or pseudohalide containing complex with the pyrimidine pyrazine or pyridazine compound in the water-immiscible organic solvent. Examples of such metals include copper, cobalt, cadmium and zinc. The process of the present invention is especially suitable for the solvent extraction of copper from aqueous solution obtained by the halide or psuedohalide leaching of sulphur containing ores, for example from solutions obtained by the leaching of ores such as chalcopyrite with aqueous ferric chloride or cupric chloride solutions.

It will be appreciated that the process of the present invention may be incorporated into a wide variety of different methods for the overall recovery of metals from their ores or from other metal-bearing sources. Details of these methods will vary depending on the metal concerned and the nature and composition of the leach solution. By way of example, an integrated process which is especially suitable for leach solutions containing high levels of cupric ion is described in European Patent Application No. 0 057 797.

The extraction process of the present invention may be represented by an equation such as the following:

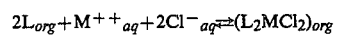

where M is a divalent metal ion such as copper or zinc.

This equation is a grossly oversimplified representation of a very complex process and is not to be taken as in any way limiting the scope of the present invention, but it serves to illustrate the formation of a neutral organic phase complex of the divalent metal and the extractant (L) which is believed to predominate in the process of the present invention. The equation illustrates the reversible nature of the extraction, whereby the complex of the metal and the extractant in the organic phase can be stripped to return the purified and concentrated metal ion into an aqueous phase. Stripping may take place for example on contact of the organic phase containing the metal/extractant complex with water or with the aqueous solution from the metal recovery (for example electrowinning) stage which is depleted in the metal and in the halide ion.

A further property which is of importance for an extractant in the process of the present invention is the absence of significant protonation by the acidic leach liquor. Such protonation may be represented by an equation such as:

$$L_{org} + H^+_{aq} + Cl^-_{aq} \rightleftarrows (LH^+Cl^-)_{org}$$

where L is the extractant. Such protonation of the ligand carries hydrochloric acid into the organic phase and builds up an excessive chloride ion concentration on the strip side. Preferred reagents of the present invention combine a high affinity for copper with an especially low acid transfer into the organic phase. Such reagents are especially useful for the treatment of metal solutions having high concentrations of acid/halide ion.

Examples of suitable water-immiscible organic solvents are aliphatic, aromatic and alicyclic hydrocarbons, chlorinated hydrocarbons such as perchloroethylene, trichloroethane and trichloroethylene. Mixtures of solvents may be used. Especially preferred in conventional hydrometallurgical practice are mixed hydrocarbon solvents such as high boiling, high flash point petroleum fractions (for example kerosene) with varying aromatic content. In general, hydrocarbon solvents having a high aromatic content, for example AROMASOL H which consists essentially of a mixture of trimethylbenzenes and is commercially available from Imperial Chemical Industries PLC (AROMASOL is a trade mark) or SOLVESSO 150 commercially available from Esso (SOLVESSO is a trade mark), provide a higher solubility for the extractant and its metal complex, whilst kerosene having a relatively low aromatic content, for example ESCAID 100 which is a petroleum distillate comprising 20% aromatics, 56.6% paraffins and 23.4% napthenes commercially available from ESSO (ESCAID is a trade mark) may in certain cases improve the hydrometallurgical performance of the extractant. Factors influencing the solubility of the extractant and its metal complex are complicated, but in general extractants having highly branched substituents and/or an isomeric mixture of substituents have comparatively high solubility. The concentration of the extractant in the water-immiscible organic solvent may be chosen to suit the particular leach solution to be treated. Typical values of extractant concentration in the organic phase are between about 0.1 to 2 Molar, and an especially convenient range is from 0.2 to 1.0 Molar in the organic solvent.

As illustrated by the examples, the extractants of the present invention provide a range of properties so that the optimum extractant may be selected for a given leach solution and extraction conditions.

In general we have found that pyrazines, and in particular those substituted pyrazines shown in the examples, have excellent properties in terms of a relatively high "strength" (ability to extract relatively high levels of copper from the leach solution) which is combined with an excellent resistance to proton transfer, even in more acidic leach solutions. In general, however, the substituted pyrazines of the invention and their metal complexes have insufficient solubility in preferred kerosene solvents having a relatively low aromatic content to operate at the higher end of the preferred range of extractant concentration. They are therefore most suitable for use at lower concentration, for example at concentrations below 0.5M, and in solvents having a higher aromatic content.

In general we have found that pyrimidines have good solubility in preferred solvents, and a good resistance to long-term hydrolysis under the stringent conditions of the solvent extraction process. The properties of individual pyrimidines may vary. Thus esters of 4-methylpyrimidine-5-carboxylic acid, for example the esters of Example 1 and 3, are excellent for use with leach solutions in the middle of the range of chloride ion concentration (for example about 4 to 7 Molar in chloride ion). Esters of 4-phenylpyrimidine-5-carboxylic acid, for example those of Example 6, are weak ligands which are especially useful for leach solutions having a high chloride ion concentration (above 7 Molar in chloride ion), particularly when the acidity is also high (0.5M and higher in HCl). Under these conditions, the ester of 4-phenylpyrimidine-5-carboxylic acid shows good copper extraction with relatively low acid transfer. The loaded extractant is readily stripped to recovery the copper.

Certain pyrimidines pyrazines and pyridazines for use in the present invention are novel compounds and the present invention includes such novel compounds.

The invention is illustrated by the following examples in which all parts and percentages are by weight unless otherwise stated.

EXAMPLE 1

The 2-hexyldecyl ester of 4-methylpyrimidine-5-carboxylic acid was prepared as follows:

The ethyl ester of 4-methylpyrimidine-5-carboxylic acid was prepared using the method described in Helv. Chim. Acta 41 1806 (1958). This product (27 g) was heated with 2-hexyldecanol (34.5 g) at 160° C. in the presence of tetrabutyl titanate (3 drops). Over the next 48 hours a further 9 drops of tetrabutyl titanate was added, and the temperature was then raised to 190° C. Heating continued for a further 23 hours. Distillation of the product gave an oil having a boiling point of 180° C. at 0.05 mm of mercury. The structure of the product was confirmed by infrared and n.m.r. analysis.

The ability of the 2-hexyldecyl ester of 4-methylpyrimidine-5-carboxylic acid to extract copper from aqueous solution containing chloride ion was investigated by the following general method:

An aqueous solution was prepared which was 0.1M in cupric chloride (6.35 gpl copper), and 0.1M in hydrochloric acid and which contained 250 gpl of calcium chloride dihydrate. This solution was then agitated for 1 minute with an equal volume of a solution which was a 0.2M solution of the extractant in SOLVESSO 150. The layers were allowed to separate and settle, and were separately analysed for copper content. The transfer of copper from the aqueous to the organic phase was calculated as the percentage of the ligand taken up as the copper complex (assuming the complex $L_2CuCl_2$). The transfer of hydrochloric acid from the aqueous solution into the organic solution was calculated as the percentage of ligand that was protonated. The test was repeated using different molarities of hydrochloric acid and different concentrations of calcium chloride. The test was then repeated using ESCAID 100 as solvent in place of SOLVESSO 15. The results are presented in Table 1. The results show that the ligand has an excellent affinity for copper combined with a low transfer of acid even at high chloride ion/acid concentrations. The ligand shows excellent copper transfer when ESCAID 100 is used as solvent.

EXAMPLE 2

The 2-hexyldecyl ester of 2,4-dimethylpyrimidine-5-carboxylic acid was prepared from the corresponding ethyl ester and 2-hexyldecanol using the method of Example 1. The compound was evaluated as an extractant for copper using the procedure of Example 1, and the results are presented in Table 1. The results show that the ligand has substantial affinity for copper.

EXAMPLE 3

The isooctadecyl ester of 4-methylpyrimidine-5-carboxylic acid was prepared from the corresponding ethyl ester and commercial isooctadecanol using the method of Example 1. The compound was evaluated as an extractant for copper using the procedure of Example 1, and the results are presented in Table 1. The results show that the ligand has good affinity for copper combined with a relatively low acid transfer even at high chloride ion/acid concentrations.

EXAMPLE 4

The good solubility and stripping properties of the product of Example 3 were demonstrated as follows:

A solution of the ligand which was 0.48 molar in ESCAID 100 was loaded until the copper concentration in the organic phase reached 13.7 gpl (90% of the theoretical maximum) by shaking with fresh portions of an aqueous solution which was 0.1 molar in $CuCl_2$ and 0.1 molar in hydrochloric acid and which contained 700 gpl $CaCl_2.2H_2O$.

The organic phase was separated from the aqueous phase and allowed to stand for 10 months at ambient temperature. No precipitation or phase separation was observed during this period. The organic phase solution was then stripped by shaking with an equal volume of water. The aqueous solution was analysed by titration, and it was found that more than 95% of the copper initially present in the loaded organic solution had transferred to the aqueous phase.

EXAMPLE 5

The 2-hexyldecyl ester of pyrazine-2-carboxylic acid was prepared as follows:

Pyrazine-2-carboxylic acid (12.4 g), thionyl chloride (17.85 g) toluene (100 ml) and dimethyl formamide (3 drops) were refluxed together for one and a half hours during which time a clear red solution formed. The solvent and excess thionyl chloride were removed under vacuum, and 2-hexyldecanol (21.8 g) was added, with the evolution of heat. The product was taken up in dichloromethane (200 ml) and the solution washed successively with water, sodium carbonate, dilute hydrochloric acid and water once more. The solution was dried over magnesium sulphate and carbon screened. On removal of the solvent the product was distilled to give 22.33 g of an oil having a boiling point of 190° C. at 0.4 mm of mercury pressure. The structure was confirmed by infrared and n.m.r. analysis.

The compound was evaluated as an extractant for copper using the procedure of Example 1, and the results are presented in Table 1. The results show that the ligand has a very good affinity for copper combined with an exceptionally low acid transfer even at high chloride ion/acid concentrations.

EXAMPLE 6

The isooctadecyl ester of pyrazine-2-carboxylic acid was prepared from pyrazine-2-carboxylic acid and isooctadecanol using the method of Example 5.

The compound was evaluated as an extractant for copper using the procedure of Example 1, and the results are presented in Table 1. The results show that the ligand has a very good affinity for copper combined with an exceptionally low acid transfer even at high chloride ion/acid concentrations.

EXAMPLE 7

(1) Preparation of Ethoxy methylene ethyl benzoylacetotate

A mixture of triethyl orthoformate (177.6 parts), ethyl benzoylacetate (192 parts) and glacial acetic acid (6 parts) was stirred and heated at 140° to 150° C. for about 4½ hours whilst the ethanol generated distilled off into a receiver. The residue was distilled and the fraction distilling at 164°–170° C. at 0.2 mm of mercury pressure, ethoxy methylene ethyl benzoylacetate (137.3 parts), was collected.

(2) Preparation of 4-phenyl-5-ethoxycarbonylpyrimidine

Formamidine acetate (57.2 parts) was added to a stirred solution of sodium (12.65 parts) in methylated spirits (234 parts) and the stirring was continued for half an hour. Ethoxy methylene ethyl benzoylacetate (124 parts) was added and the temperature was allowed to rise to 40° to 50° C. The mixture was heated under reflux for 2 hours and the solvent was then distilled off. The residue was distilled and the fraction boiling at 122° to 132° C. under 0.2 mm of mercury pressure, 4-phenyl-5-ethoxycarbonylpyrimidine (77.8 parts), was collected.

(3) Preparation of the isooctadecyl ester of 4-phenylpyrimidine-5-carboxylic acid A mixture of 4-phenyl-5-ethoxycarbonylpyrimidine (68.4 parts), isooctadecanol (85.05 parts) and tetrabutyltitanate (0.85 parts) was stirred and heated at 160° C. to 170° C. for 48 hours, allowing the ethanol produced to distil off. Excess alcohol was removed and the product (120 parts) was the isodecyl ester of 4-phenylpyrimidine-5-carboxylic acid.

The product was evaluated as an extractant for copper using the procedure of Example 1, and the results are presented in Table 1. The results show that this compound is a "weak" ligand which has good resistance to acid transfer, and is especially suitable for use with feed solutions of high chloride ion concentration.

In a further test to evaluate the use of the ligand in more concentrated solution in the water-immiscible solvent, a 0.5 Molar solution of the product in ESCAID 100 was twice contacted with portions of an aqueous feed at an organic:aqueous ratio of 1:2. The aqueous feed solution had high acidity and high chloride ion concentration, and was prepared by dissolving cupric chloride dihydrate (13.4 g), calcium chloride dihydrate (57.7 g) and 10M hydrochloric acid (b 5.0 cm$^3$) in water and adjusting the volume to 100 cm$^3$. The organic solution was analysed after the extraction and was found to contain 12.9 gpl of copper (81% of the theoretical maximum uptake). The clear greenish blue loaded organic solution showed no precipitation of insoluble matter on standing for a period of 5 months.

EXAMPLE 8

A 0.5 molar solution in ESCAID 100 of 4-phenylpyrimidine-5-carboxylic acid (prepared as in Example 7) was used to extract copper to a loading of 12.57 gpl (as $CuCl_2$). The loaded extractant solution was stripped by equilibration with an aqueous solution containing 27.26 gpl copper (as CuCl$_2$) and 5 gpl hydrochloric acid. At a ratio of organic phase to aqueous phase of 1:1 by volume, the equilibrium copper concentrations were: 0.57 gpl of copper in the organic phase and 39.39 gpl copper in the aqueous phase. At a ratio of organic phase to aqueous phase of 2:1 by volume, the equilibrium copper concentrations were: 0.89 gpl of copper in the organic phase and 50.45 gpl copper in the aqueous phase.

EXAMPLE 9

A 0.5 molar solution in ESCAID 100 of 4-phenylpyrimidine-5-carboxylic acid (prepared as in Example 7) was used to extract copper to a loading of 11.50 gpl (as CuCl$_2$). The loaded extractant solution was stripped by equilibration with an aqueous soluton containing 1.0 gpl copper (as CuCl$_2$) 58.5 gpl sodium chloride and 1 gpl hydrochloric acid. At a ratio of organic phase to aqueous phase of 1:1 by volume, the equilibrium copper concentrations were: 0.25 gpl of copper in the organic phase and 12.26 gpl copper in the aqueous phase. At a ratio of organic phase to aqueous phase of 2:1 by volume, the equilibrium copper concentrations were: 0.64 gpl of copper in the organic phase and 22.68 gpl copper in the aqueous phase.

EXAMPLE 10

The 3,9-diethyl-6-tridecyl ester of pyrazine-2-carboxylic acid was prepared from pyrazine-2-carboxylic acid and 3,9-diethyl-tridecan-6-ol (a secondary alcohol) using the general method of Example 5. The product had a boiling range of 165° to 170° C. at 0.2 mm of mercury pressure.

The product was evaluated as an extractant for copper using the procedure of Example 1, and the results are presented in Table 1.

EXAMPLE 11

N,N-bis(2'-ethylhexyl)pyrazine-2-carboxamide was prepared from pyrazine-2-carboxylic acid and bis(2-ethylhexyl)amine by the general method of Example 5, the amine being used in place of the alcohol. The compound had a boiling range of 155° to 160° C. at 0.2 mm pressure of mercury.

The product was evaluated as an extractant for copper using the procedure of Example 1, and the results are presented in Table 1.

EXAMPLE 12

N,N-diisononylpyrazine-2-carboxamide was prepared from pyrazine-2-carboxylic acid and commercial di-isononylamine using the general method of Example 11. The product had a boiling range of 163°-165°° C. at 0.15 mm of mercury pressure.

The product was evaluated as an extractant for copper using the precedure of Example 1, and the results are presented in Table 1.

EXAMPLE 13

The tridecyl ester of 4-phenylpyrimidine-5-carboxylic acid was prepared from 4-phenyl-5-ethoxycarbonylpyrazine and commercial tridecanol using the general procedure of Example 7. The product had a boiling range of 160°-170° C. at 0.2 mm pressure of mercury.

The product was evaluated as an extractant for copper using the procedure of Example 1, and the results are presented in Table 1.

EXAMPLE 14

The 2-hexyldecyl ester of 4-phenylpyrimidine-5-carboxylic acid was prepared from 2-hexyldecanol and 4-phenyl-5-ethoxycarbonylpyrimidine using the general procedure of Example 7. The product had a boiling range of 206°-208° C. at 0.2 mm pressure of mercury.

The product was evaluated as an extractant for copper using the procedure of Example 1, and the results are presented in Table 1.

EXAMPLE 15

The isooctadecyl ester of 4-(4'-methoxyphenyl)-pyrimidine-5-carboxylic acid was prepared using the general method of Example 7 from 4-methoxybenzoyl chloride, ethyl acetoacetate and sodium hydroxide via the intermediates ethyl (4-methoxybenzyl)acetate and the ethyl ester of 4-(4'-methoxyphenyl)pyrimidine-5-carboxylic acid. The product had a boiling point of 200° to 205° C. at 0.1 mm of mercury pressure. The product was evaluated as an extractant for copper using the procedure of Example 1 and the results are presented in Table 1.

EXAMPLE 16

The isooctadecyl ester of 4-(2'-chlorophenyl)pyrimidine-5-carboxylic acid was prepared using the general method of Example 7 from 2-chlorobenzoyl chloride, ethyl acetoacetate and sodium hydroxide via the intermediates ethyl (2-chlorobenzoyl)acetate and the ethyl ester of 4-(2'-chlorophenyl)pyrimidine-5-carboxylic acid. The product had a boiling point of 192° C. at 0.1 mm of mercury pressure. The product was evaluated as an extractant for copper using the procedure of Example 1 and the results are presented in Table 1.

EXAMPLE 17

The isooctadecyl ester of 4-carboxypyridazine was prepared as follows:

4,5-Dicarboxypyridazine (12 parts), isooctadecanol (50 parts), toluene (20 parts) and 4-methylbenzene sulphonic acid (2 parts) were stirred and boiled under reflux below a Dean-Stark trap initially filled with toluene. With these proportions of reactants, the temperature of the reaction mixture was 148° C. and partial decarboxylation as well as esterification of the acid took place. After 1.5 hours, when 0.75 ml of water had collected in the trap, the reaction mixture was cooled, diluted with petroleum ether (b.p. 60°-80° C., 50 parts) and washed with water. The product was distilled under reduced pressure and the fraction distilling at 180°-190° C. at 0.4 mercury pressure was collected. 3.6 parts of product were obtained having a purity of 84% as measured by potentiometric titration with perchloric acid in acetic acid/acetic anhydride medium. The product was evaluated as an extract and using the method of Example 1, and the results are listed in Table 1.

EXAMPLE 18

The isodecyl ester of 4-carboxypyridazine was prepared using the general method of Example 17 from isodecanol and 4,5-dicarboxypyridazine. The product has a boiling range of 150°-160° C. at 0.4 mm of mercury pressure. The product was evaluated as an extractant for copper by the procedure of Example 1, and the results are listed in Table 1. The results show that this compound has inferior solubility to the corresponding isooctadecyl ester of Example 17.

EXAMPLE 19

The bis(isodecyl)ester of 4,5-dicarboxypyridazine was prepared as follows:

4,5-dicarboxypyridazine (16 parts), isodecanol (70 Parts), toluene (50 parts) and 4-methylbenzene sulphonic acid (2.5 parts) were stirred and heated for 5 hours under reflux below a Dean-Stark trap initially filled with toluene. With these proportions the reaction temperature was 128° C., and 1.6 parts of water collected in the trap. The mixture was cooled, diluted with petroleum spirit (70 parts b.p. 60°-80° C.), washed with water and distilled under reduced pressure. A small quantity of the isodecyl ester of 4-carboxypyridazine boiling at 155° C. at 0.4 mm of mercury pressure was collected and this was followed by the bis(isodecyl)ester of 4,5-dicarboxypridazine boiling at 235°-240° C. at a pressure of 0.4 mm of mercury. The product (5.6 parts) had a purity of 98% as estimated by titration with perchloric acid and was evaluated as an extractant for copper using the procedure of Example 1. The results are listed in Table 1.

EXAMPLE 20

The ease with which the compounds of the invention may in general be stripped of copper was demonstrated as follows:

A 0.2 molar solution in SOLVESSO 150 of the respective ligands of Examples 7, 10, 11, 14, 16 and 17 was loaded by contacting with an equal volume of 0.1 molar aqueous $CuCl_2$ which was 0.1 molar in hydrochloric acid and contained 700 gpl $CaCl_2.2H_2O$. The resultant loading were as recorded in the appropriate column of Table 1. The loaded organic phase was separated and shaken with an equal volume of water, and the water layer was analysed for copper. In every case, more than 97% of the copper originally present in the loaded organic phase was found to have transferred into the aqueous phase.

TABLE 1

| Example | HCl Molarity | $CaCl_2.2H_2O$ (g/l) | % Uptake from 0.1M $CuCl_2$ Copper | protonation |
|---|---|---|---|---|
| 1. | 0.1 | 250 | 18 | 0 |
| (Solvent: | 0.1 | 500 | 42 | 0 |
| SOLVESSO | 0.1 | 700 | 63.5 | 0.5 |
| 150) | 1.0 | 250 | 32 | 0.5 |
|  | 1.0 | 500 | 53 | 2 |
|  | 1.0 | 700 | 61 | 27 |
| 1. | 0.1 | 250 | 24 | 0 |
| (Solvent: | 0.1 | 700 | 70 | 0 |
| ESCAID | 1.0 | 250 | 39 | 0 |
| 100) | 1.0 | 700 | 65 | 31 |
| 2. | 0.1 | 700 | 22 | 13 |
| (Solvent: SOLVESSO 150) | 1.0 | 700 | 53 | 82 |
| 3. | 0.1 | 700 | 55 | 2 |
| (Solvent: | 1.0 | 350 | 21 | 1 |
| SOLVESSO 150) | 1.0 | 700 | 55 | 21 |
| 5. | 0.1 | 700 | 43 | 0 |
| (Solvent: | 1.0 | 250 | 14 | 0 |
| SOLVESSO 150) | 1.0 | 700 | 47 | 0.5 |
| 6. | 0.1 | 700 | 39 | 0 |
| (Solvent: | 1.0 | 250 | 10 | 0 |
| SOLVESSO 150) | 1.0 | 700 | 43 | 1 |
| 7. | 0.1 | 250 | 4 | 0 |
| (Solvent: | 0.1 | 700 | 37 | 1.5 |
| SOLVESSO | 1.0 | 250 | 6 | 0 |
| 150) | 1.0 | 700 | 41 | 9 |
| 7. | 0.1 | 250 | 2 | 0.5 |
| (Solvent: | 0.1 | 700 | 51 | 1 |
| ESCAID | 1.0 | 250 | 6 | 0.5 |
| 100) | 1.0 | 700 | 55 | 7.5 |
| 10. | 0.1 | 250 | 6 | 0 |
| (Solvent: | 0.1 | 700 | 46 | 0 |
| SOLVESSO | 1.0 | 250 | 12 | 0 |
| 150) | 1.0 | 700 | 49 | 1.5 |
| 11. | 0.1 | 250 | 0 | 0.25 |
| (Solvent: | 0.1 | 700 | 41 | 0.25 |
| SOLVESSO | 1.0 | 250 | 4 | 0.25 |
| 150) | 1.0 | 700 | 47 | 5.5 |
| 12. | 0.1 | 250 | 10 | 0.25 |
| (Solvent: SOLVESSO 150) | 1.0 | 700 | 85 | 11 |
| 13. | 0.1 | 250 | 2 | 0 |
| Solvent: SOLVESSO 150) | 1.0 | 700 | 47 | 12 |
| 14. | 0.1 | 250 | 3 | 0 |
| (Solvent: SOLVESSO 150) | 1.0 | 700 | 47 | 9 |
| 15. | 0.1 | 250 | 3 | 0 |
| (Solvent: SOLVESSO 150) | 1.0 | 700 | 58 | 8 |
| 16. | 0.1 | 250 | 0 | 0 |
| (Solvent: | 0.1 | 700 | 16 | 0.5 |
| SOLVESSO | 1.0 | 250 | 2 | 0 |
| 150) | 1.0 | 700 | 20 | 2.5 |
| 17. | 0.1 | 250 | 11 | 0 |
| (Solvent: | 0.1 | 700 | 86 | 1 |
| SOLVESSO 150) | 1.0 | 700 | 80 | 41 |
| 18. | 0.1 | 250 | 16 | 0 |
| (Solvent: SOLVESSO 150) | 0.1 | 700 | third liquid phase formed | |
| 19. | 0.1 | 250 | 7 | 0 |
| (Solvent: | 0.1 | 700 | 67 | 2 |
| SOLVESSO 150) | 1.0 | 700 | 57 | 15 |

I claim:

1. A process for extracting metal values from aqueous solutions of metal salts containing halides or pseudo halide anions which comprises contacting the aqueous solution with a solution in a water-immiscible organic solvent of a substituted pyrimidine, pyrazine or pyridazine of formula:

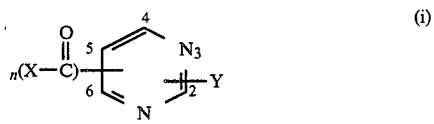

(i)

or

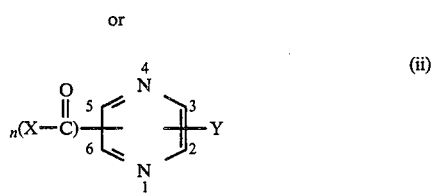

(ii)

or

-continued

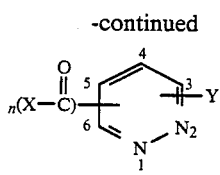
(iii)

wherein

X is the group —OR$_1$ or —NR$_2$R$_3$, R$_1$ being a hydrocarbyl group containing from 1 to 36 carbon atoms and R$_2$ and R$_3$ separately being hydrogen or a hydrocarbyl group, and R$_2$ and R$_3$ together containing from 1 to 36 carbon atoms;

n is 1, 2 or 3; and

Y represents one or more optionally substituted phenyl groups, provided that there is present in the molecule a total number of from 5 to 36 alkyl carbon atoms.

2. A process according to claim 1 wherein Y represents a phenyl group having one or more substituents selected from the group consiting of a lower alkyl group, a lower alkoxy group, a carboxylic acid group, a carboxylic acid ester group and a halogen atom.

3. A process according to claim 1 or claim 2 wherein there is present in the molecule a total number of from 9 to 24 alkyl carbon atoms.

4. A process according to claim 1 or claim 2 wherein n is 1, X is the group —OR$_1$ and R$_1$ is a branched chain alkyl group containing from 9 to 24 carbon atoms.

5. A process according to claim 1 or 2 wherein n is 1 or 2, X is the group —OR$_1$ and R$_1$ is the group

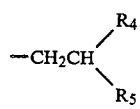

wherein R$_4$ and R$_5$ are alkyl groups and R$_4$ contains two fewer carbon atoms than R$_5$.

6. A process according to claim 1 or claim 2 wherein n is 1, X is the group —OR$_1$, and R$_1$ is isodecyl, tridecyl, 2-hexyldecyl, isooctadecyl or 3,9-diethyl-6-tridecyl.

7. A process according to claim 1 or claim 2 wherein there is employed a substituted pyrimidine; n is 1; the group —COX is located in the -5 position on the pyrimidine ring; and the group —Y is located in the -4 position.

8. A process according to claim 1 wherein n is 1, X is the group —NR$_2$R$_3$, and R$_2$ and R$_3$ are alkyl groups which taken together contain a total of from 15 to 36 carbon atoms.

* * * * *